United States Patent
Witt et al.

(10) Patent No.: US 10,584,096 B2
(45) Date of Patent: Mar. 10, 2020

(54) CYCLIC IMIDE SLURRY COMPOSITIONS

(71) Applicant: ExxonMobile Chemical Patents Inc., Baytown, TX (US)

(72) Inventors: Andrew R. Witt, Huffman, TX (US); Christopher L. Becker, Manhattan, KS (US); Bryan A. Patel, Jersey City, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/338,827

(22) PCT Filed: Sep. 18, 2017

(86) PCT No.: PCT/US2017/051989
§ 371 (c)(1),
(2) Date: Apr. 2, 2019

(87) PCT Pub. No.: WO2018/075176
PCT Pub. Date: Apr. 26, 2018

(65) Prior Publication Data
US 2019/0233373 A1    Aug. 1, 2019

Related U.S. Application Data

(60) Provisional application No. 62/409,719, filed on Oct. 18, 2016.

(51) Int. Cl.
| | | |
|---|---|---|
| *C07C 407/00* | (2006.01) | |
| *C07C 29/50* | (2006.01) | |
| *C07C 45/39* | (2006.01) | |
| *C07C 2/74* | (2006.01) | |
| *C07C 45/33* | (2006.01) | |
| *B01J 31/02* | (2006.01) | |
| *C07C 35/08* | (2006.01) | |
| *C07C 39/04* | (2006.01) | |
| *C07C 49/403* | (2006.01) | |
| *C07C 409/08* | (2006.01) | |
| *C07C 409/14* | (2006.01) | |

(52) U.S. Cl.
CPC ......... *C07C 407/00* (2013.01); *B01J 31/0247* (2013.01); *C07C 29/50* (2013.01); *C07C 45/33* (2013.01); *C07C 45/39* (2013.01); *B01J 2231/70* (2013.01); *C07C 35/08* (2013.01); *C07C 39/04* (2013.01); *C07C 49/403* (2013.01); *C07C 409/08* (2013.01); *C07C 409/14* (2013.01); *C07C 2601/14* (2017.05); *C07C 2601/16* (2017.05); *Y02P 20/125* (2015.11)

(58) Field of Classification Search
CPC ....... C07C 407/00; C07C 29/50; C07C 45/39; C07C 2/74
See application file for complete search history.

(56) References Cited

U.S. PATENT DOCUMENTS

| | | | |
|---|---|---|---|
| 3,351,426 A | 11/1967 | Leaver et al. | |
| 4,956,168 A | 9/1990 | Wagaman | |
| 5,472,679 A | 12/1995 | Levinthal et al. | |
| 6,299,734 B1 | 10/2001 | Watzenberger et al. | |
| 6,316,639 B1 | 11/2001 | Fritz-Langhals | |
| 6,528,658 B1 * | 3/2003 | Miura .................... | B01J 31/006 548/466 |
| 7,396,519 B2 | 7/2008 | Lin | |
| 7,582,774 B2 | 9/2009 | Kajikawa | |
| 2013/0203984 A1 | 8/2013 | Becker et al. | |
| 2013/0211036 A1 | 8/2013 | Dakka et al. | |
| 2014/0148569 A1 | 5/2014 | Dakka et al. | |
| 2014/0316098 A1 * | 10/2014 | Wang ..................... | B01J 29/08 528/332 |

FOREIGN PATENT DOCUMENTS

| | | |
|---|---|---|
| CN | 1051170 | 5/1991 |
| CN | 101845012 | 9/2010 |
| DE | 3528463 | 2/1987 |
| DE | 3601803 | 7/1987 |
| EP | 0108294 | 8/1986 |

(Continued)

OTHER PUBLICATIONS

Takahiro Iwahama et al: "Production of Hydrogen Peroxide via Aerobic Oxidation of Alcohols Catalyzed by N-Hydroxyphthalimide", Organic Process Research and Development, vol. 4, No. 2, Mar. 2000 (Mar. 1, 2000), US, pp. 94-97, XP055426228, ISSN: 1083-6160, DOI: 10.1021/op990082f.

Huang et al.: "Catalytic performance of N-hydroxyphthalimide-immobilized cross-linked polystyrene microspheres in oxidation of toluene and cyclohexanol", The Chinese Journal of Process Engineering, vol. 14, No. 4, Aug. 2014 (Aug. 1, 2014), pp. 683-688.

Guha et al.: "Aerobic Oxidation of Cyclohexane using N-Hydroxyphthalimide Bearing Fluoroalkyl Chains", Adv. Synthesis & Catalysis, vol. 350, No. 9, Jun. 2008 (Jun. 1, 2008), pp. 1322-1330.

*Primary Examiner* — Sikarl A Witherspoon
(74) *Attorney, Agent, or Firm* — Kevin M. Faulkner

(57) ABSTRACT

Provided herein is a cyclic imide slurry composition and processes for forming and/or using such a composition. The slurry composition comprises solid cyclic imide and organic liquid, such as liquid alkylbenzene, liquid cyclohexane, and/or liquid organic alcohol (such as cyclohexanol). The slurry composition may find particular use in processes in which the cyclic imide serves as an oxidation catalyst (e.g., as a radical initiator). For instance, the slurry composition may be useful in the oxidation of a liquid alkylbenzene such as cyclohexylbenzene to corresponding 1-cyclohexyl-1-phenyl hydroperoxide. Such an oxidation reaction may further be part of an integrated process for the production of phenol and/or cyclohexanone from benzene via hydroalkylation to form cyclohexylbenzene.

19 Claims, 6 Drawing Sheets

(56) References Cited

FOREIGN PATENT DOCUMENTS

| | | |
|---|---|---|
| JP | 2001-233854 | 8/2001 |
| JP | 2002-047270 | 2/2002 |
| JP | 2003-081941 | 3/2003 |
| JP | 2003-128602 | 5/2003 |
| JP | 2002-128760 | 2/2004 |
| JP | 2004-51626 | 2/2004 |
| WO | 95/25090 | 9/1995 |
| WO | 97/22551 | 6/2001 |
| WO | 2009/131769 | 10/2009 |
| WO | 2010/042273 | 4/2010 |
| WO | 2010/098916 | 9/2010 |
| WO | 2012/145030 | 10/2012 |
| WO | 2014/137623 | 9/2014 |
| WO | 2016/053583 | 4/2016 |

\* cited by examiner

US 10,584,096 B2

CYCLIC IMIDE SLURRY COMPOSITIONS

PRIORITY CLAIM

This application is a National Phase Application claiming priority to PCT Application Serial No. PCT/US2017/051989, filed Sep. 18, 2017, which claims priority to and the benefit of U.S. Ser. No. 62/409,719, filed Oct. 18, 2016 and is incorporated by reference in its entirety.

FIELD

The present invention relates to processes, systems, and apparatus for making compositions of cyclic imide oxidation catalyst, and in particular slurries of solid cyclic imide oxidation catalyst. A particular example of solid cyclic imide oxidation catalyst is N-hydroxyphthalimide (NHPI). The slurries may be particularly useful for delivering the oxidation catalyst to a mixed-phase (e.g., a vapor/liquid) oxidation reaction system. Of particular interest is the oxidation of cyclohexylbenzene to form cyclohexylbenzene hydroperoxide. Such an oxidation reaction may be employed as part of a process for making cyclohexanone and/or phenol from benzene via hydroalkylation to cyclohexylbenzene.

BACKGROUND

Cyclic imide compounds, and in particular N-Hydroxyphthalimide (NHPI) have many potential uses. In particular, they have shown promise as radical mediators in a number of radical based oxidation reactions, such that these compounds can be used to catalyze oxidation reactions of hydrocarbons. For instance, cyclic imides such as NHPI are useful in the oxidation of cyclohexane to cyclohexanone and/or cyclohexanone. Another example is the oxidation of alkylbenzenes (such as, e.g., cyclohexylbenzene, also referred to herein as "CHB") to corresponding alkylbenzene-hydroperoxides (in particular, oxidation of cyclohexylbenzene to cyclohexyl-1-phenyl-1-hydroperoxide, referred to herein as "cyclohexylbenzene-hydroperoxide" or "CHB-HP"). As described previously (e.g., in US 2014/0148569, US 2013/0211036, and US 2013/0203984), NHPI-catalyzed oxidation of cyclohexylbenzene is particularly advantaged in a process for making cyclohexanone from benzene via: (i) hydroalkylation of the benzene to cyclohexylbenzene; (ii) oxidation of the cyclohexylbenzene to cyclohexylbenzene-hydroperoxide; and (iii) cleavage of the cyclohexylbenzene-hydroperoxide to phenol and cyclohexanone.

Oxidation of hydrocarbons (e.g., cyclohexane and/or alkylbenzenes) may preferably be a gas-liquid oxidation that takes place through a free radical chain reaction homogeneously catalyzed by the cyclic imide (e.g., NHPI), for instance as described in WO 2014/137623 with respect to the alkylbenzene cyclohexylbenzene. In particular, the liquid-phase reaction medium comprising the cyclohexylbenzene is contacted with an oxygen-containing gas (e.g., air or $O_2$) to form the CHB-HP. However, many of the most suitable cyclic imides to catalyze the free radical chain reaction, such as NHPI, are solids.

Cyclic imides such as NHPI have also been reported as useful in the oxidation of cyclohexanol to cyclohexanone; and/or the oxidation of cyclohexane to cyclohexanol and/or cyclohexanone. See, e.g., Huang et al., "Catalytic performance of N-hydroxyphthalimide-immobilized cross-linked polystyrene microspheres in oxidation of toluene and cyclohexanol," *The Chinese Journal of Process Engineering* 14(4):683-688 (August 2014); Guha et al., "Aerobic Oxidation of Cyclohexane using N-Hydroxyphthalimide Bearing Fluoroalkyl Chains," *Adv. Synthesis & Catalysis* 350(9): 1323-1330 (June 2008).

What is needed, therefore, is a mechanism for the satisfactory delivery of solid cyclic imide to the oxidation reaction that is suitable for relatively high throughput rates desired in an industrial-scale oxidation reaction.

Some further references of potential interest in this regard may include: U.S. Pat. Nos. 4,956,168, 5,472,679, 6,299,734, 6,316,639, 7,396,519, and 7,582,774; EP Patent Publication 108294 A, German patent publications DE-A-1247282, DE-A-3528463, and DE-A-3601803; Japanese patent publications JP 2001-233854, JP 2002-047270, JP 2002-128760, JP 2003-081941, and JP 2004-051626; Chinese patent publications CN1051170, CN101845012; and WIPO Publication Nos. WO 95/25090, WO 97/22551, WO 2014/137623, and WO 2016/053583. None of these references addresses the need for efficient, safe, and readily controlled delivery of solid cyclic imides to liquid and/or gas-phase oxidation reactions at an industrial scale.

SUMMARY

Direct delivery of solid cyclic imide catalyst to a mixed-phase oxidation reaction zone presents many challenges. Direct dispensation of dry cyclic imide (e.g., NHPI) is problematic, as the dry solid could become suspended in the vapor and plug any of numerous portions of the reactor system (e.g., an offgas system drawn from the vapor phase overhead within the reaction zone, and/or pressure safety devices in the reaction zone).

Direct delivery of the dry solids to a liquid feed stream, or into a portion of the reaction zone in which liquid-phase reaction medium is present, is also undesired. Such direct delivery could, among other things: (1) result in inferior mixing of the solid catalyst particles in the liquid feed; and/or (2) create significant safety and logistical issues associated with conveying the solid to the liquid feed and/or liquid-phase reaction medium in the oxidation reaction zone. For instance, NHPI is classified as an explosive dust; it further is known to be an industrial hygiene issue because it can cause allergic reactions in some people upon contact, such as rashes, breathing issues, and the like. While the problems of (2) could be alleviated by use of, e.g., an inert carrier gas (e.g., nitrogen), delivering both the solid and carrier gas directly to the liquid feed, or directly into a liquid- and/or gas-phase reaction medium within an oxidation reactor during its normal operation, this would lead to the need to separate the inert carrier from the desired oxidation products. It could also require uneconomical reactor sizing to accommodate the additional mass flow.

The present inventors have found that, advantageously, one may form a slurry comprising the solid cyclic imide and the liquid organic material (e.g., liquid alkylbenzene) to be oxidized. This slurry, in turn, may be provided to an oxidation reaction zone (e.g., to the liquid-phase feed to the oxidation reaction zone, and/or to the liquid-phase reaction medium within the oxidation reaction zone).

In some aspects, the present invention relates to cyclic imide slurry compositions and processes for forming and/or using such compositions. The slurry composition may comprise a solid cyclic imide in an organic liquid, such as a liquid alkylbenzene. The cyclic imide may be particularly useful as an oxidation catalyst (e.g., by radical chain initiation), and in some embodiments, the organic liquid advantageously comprises, consists essentially of, or consists of the compound to be oxidized. Thus, processes of some embodiments include forming a slurry comprising solid cyclic imide in organic liquid (such as liquid alkylbenzene), providing the slurry and an oxygen-containing gas to an oxidation reaction zone, and therein oxidizing at least a portion of the organic liquid. In particular embodiments, the organic liquid is oxidized to a corresponding hydroperoxide. For instance, where the organic liquid comprises a liquid alkylbenzene such as cyclohexylbenzene, the liquid is preferably oxidized to a corresponding hydroperoxide, such as 1-cyclohexyl-1-phenyl hydroperoxide.

According to some aspects, the slurry may be formed by feeding the solid cyclic imide and organic liquid, such as liquid alkylbenzene, to a mixing device, and therein forming the slurry. The slurry in some embodiments may comprise 3 wt % to 45 wt % solid cyclic imide. In yet other embodiments, the slurry may be formed from solid cyclic imide and a liquid hydrocarbon such as cyclohexane, and/or from solid cyclic imide and an organic alcohol (especially a $C_3$ to $C_{10}$ organic alcohol such as cyclohexanol).

Furthermore, in particular aspects, the organic liquid is cyclohexylbenzene, the corresponding peroxide is 1-cyclohexyl-1-phenyl hydroperoxide, and the oxidation is part of an integrated process for making cyclohexanone and/or phenol from benzene. Such processes may include hydroalkylating benzene and hydrogen to form cyclohexylbenzene; forming a slurry from at least a portion of the cyclohexylbenzene and a solid cyclic imide; providing the slurry and an oxygen-containing gas to an oxidation reaction zone and therein oxidizing at least a portion of the cyclohexylbenzene to 1-cyclohexyl-1-phenyl hydroperoxide; and cleaving at least a portion of the 1-cyclohexyl-1-phenyl hydroperoxide to phenol and cyclohexanone.

In yet other aspects, the organic liquid is cyclohexane; or, alternatively, cyclohexanol. The slurry comprising cyclohexane and solid cyclic imide is provided to an oxidation reaction zone wherein the cyclohexane is oxidized to cyclohexanone and/or cyclohexanol. Alternatively, the slurry comprising cyclohexanol and solid cyclic imide is provided to an oxidation reaction zone wherein the cyclohexanol is oxidized to cyclohexanone.

DETAILED DESCRIPTION

Figure 1:
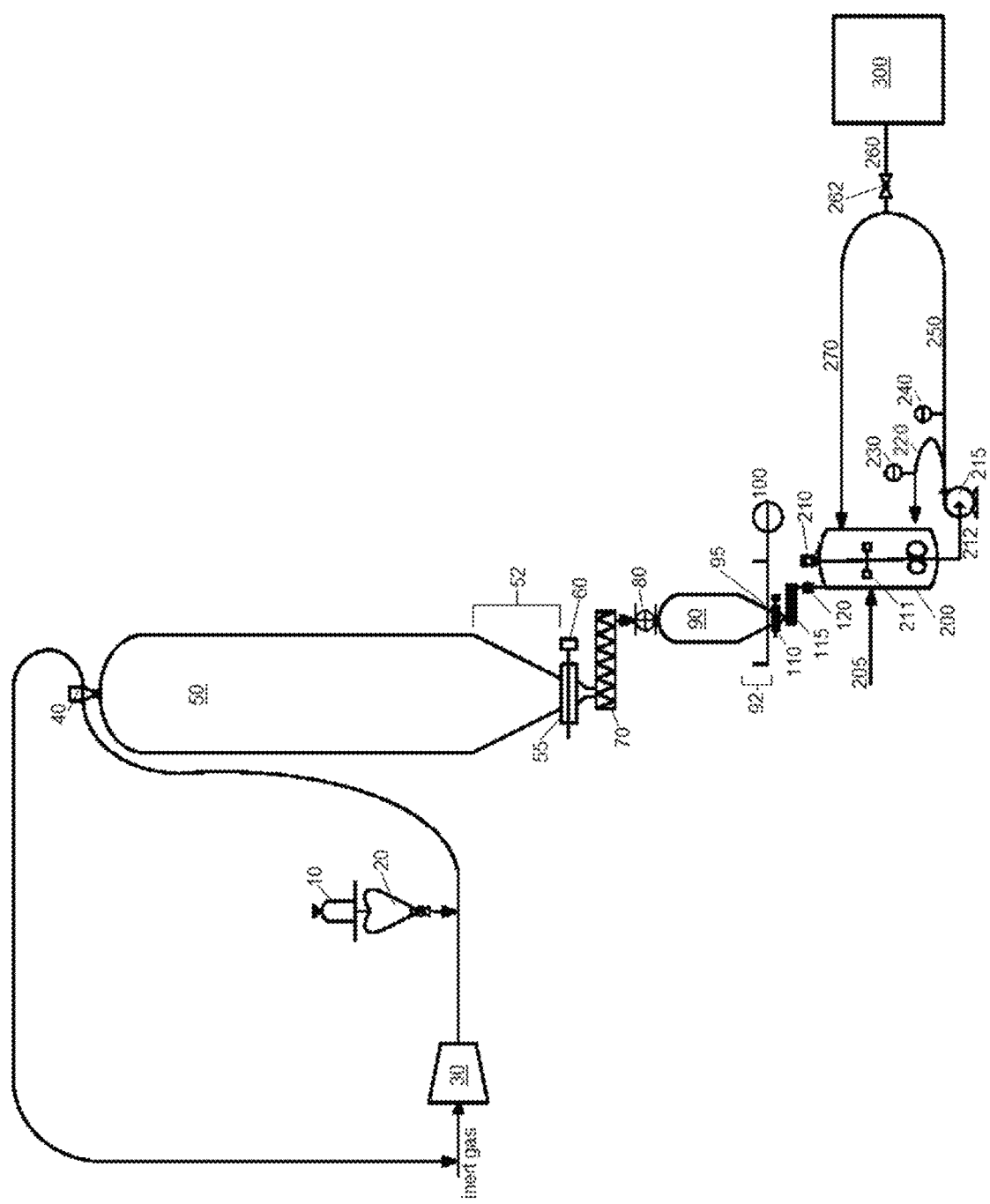
FIG. 1 is a schematic diagram of a process and system for slurrying solid cyclic imide in accordance with some embodiments.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first mixture are expressed based on the total weight of the first mixture. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

Various embodiments described herein provide a process for making a slurry of a solid cyclic imide, such as N-hydroxyphthalimide (NHPI), and for using such a slurry. The cyclic imide slurry may be provided to an oxidation reaction, particularly oxidation of an alkylbenzene such as CHB. Such processes may generally include one or more of the following: (1) forming a slurry comprising the solid cyclic imide and liquid-phase alkylbenzene; (2) providing the slurry to a mixed gas/liquid oxidation reaction zone; (3) providing additional liquid-phase alkylbenzene and an oxygen-containing gas to the mixed gas/liquid oxidation reaction zone; and (4) oxidizing at least a portion of the alkylbenzene in the mixed gas/liquid oxidation reaction zone, in the presence of the cyclic imide. Each of the aforementioned elements of such processes is discussed in further detail below.

Slurries of Solid Cyclic Imide

Solid cyclic imide, as noted, is particularly suitable to catalyze the oxidation of organic compounds (such as alkylbenzenes) by free-radical chain reaction. In the preferred case of mixed-phase oxidation, a liquid feed comprising alkylbenzene is provided to an oxidation reaction zone where it forms a liquid-phase reaction medium. An oxygen-containing gas is also provided to the oxidation reaction zone, where it is contacted with the liquid-phase reaction medium. A bubble-column reactor, stirred tank reactor, or other reactor may be a suitable oxidation reaction zone for such processes. In particular instances, the gas may be distributed through the liquid-phase reaction medium in a lower portion of the oxidation reaction zone, and a vapor-phase overhead formed within the reaction zone.

However, as previously noted, direct delivery of the solid cyclic imide catalyst to the mixed-phase reaction zone is difficult. As noted, the present inventors address the issue through, e.g., formation of a slurry comprising the solid cyclic imide and the liquid organic material (e.g., liquid alkylbenzene) to be oxidized. This slurry, in turn, may be provided to an oxidation reaction zone (e.g., to the liquid-phase feed to the oxidation reaction zone, and/or to the liquid-phase reaction medium within the oxidation reaction zone).

Preferably, the slurry is formed by providing dry cyclic imide and liquid alkylbenzene to a mixing device. The mixing device is any device suitable for forming a slurry, and may be, e.g., a slurry mix tank. More generally, the mixing device may be a vessel, preferably a vertical vessel, that contains an agitator with one or more impellers and one or more baffles protruding from an inside wall of the vessel. The device preferably further includes a recirculating fluid conduit capable of recirculating the slurry out of and into the mixing vessel (e.g., by use of a fluid pump). The device is intended to thoroughly mix the solids in the liquid vertically and axially, and further to prevent the solids from settling to the bottom of the vessel.

If the cyclic imide concentration in the slurry is too high, it may be difficult to transport the slurry (e.g., by pumping), such that the slurry is no longer readily transported, and/or such that it potentially plugs. On the other hand, it would be just as undesirable to obtain a slurry with too little cyclic imide in the alkylbenzene. That is, with too great a ratio of alkylbenzene to cyclic imide in the slurry, the oxidation reaction will tend to proceed less efficiently (due to the presence of excess alkylbenzene to be oxidized, as compared to cyclic imide catalyst).

Accordingly, in preferred embodiments, the slurry composition comprises 3 to 45 wt %, such as 5 to 35 wt % or 5 to 30 wt %, preferably 10 to 30 wt %, more preferably 10 to 20 wt %, cyclic imide in the liquid alkylbenzene, with ranges from any of the foregoing low ends to any of the foregoing high ends also contemplated in various embodiments. In some embodiments, the balance of the slurry is preferably the liquid alkylbenzene, although in some embodiments, up to 0.1, 0.5, 1, 2, or 3 wt % of impurities may be present in the slurry. An "impurity" in the context of the cyclic imide/liquid alkylbenzene slurry refers to any compound other than the cyclic imide or the liquid alkylbenzene. Thus, in various embodiments, the slurry may be characterized as comprising liquid alkylbenzene within the range from 55 to 97 wt %, such as 65 to 95 wt % or 70 to 95 wt %, preferably 70 to 90 wt %, more preferably 80 to 90 wt %, with ranges from any of the foregoing low ends to any of the foregoing high ends also contemplated in various embodiments. Certain embodiments provide processes that include maintaining cyclic imide concentration and/or maintaining liquid alkylbenzene concentration in the slurry within any of the foregoing respective ranges.

Figure 2:
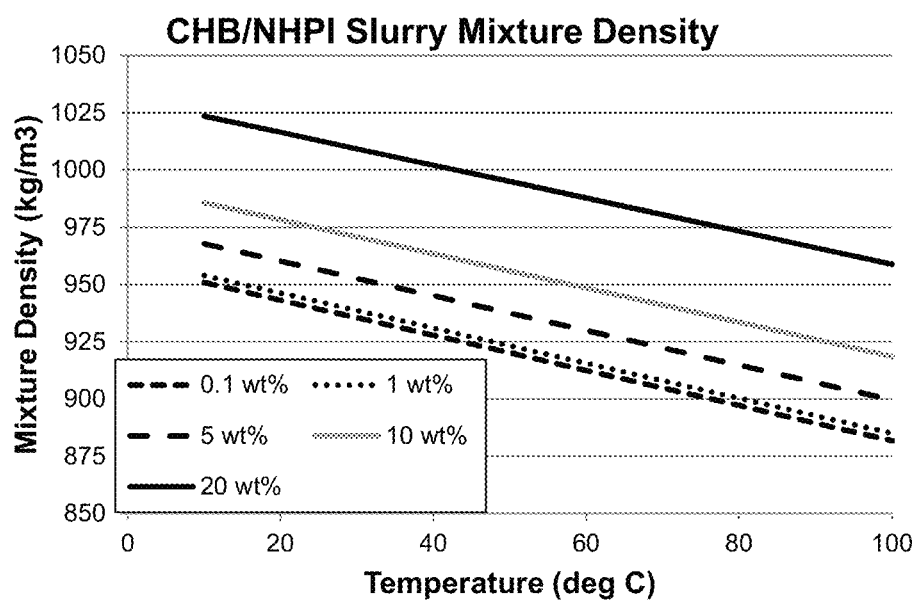
FIG. 2 is a plot of density vs. temperature for NHPI-in-CHB slurries of various concentrations of NHPI, in accordance with some embodiments.

The cyclic imide slurry's density will depend upon the cyclic imide concentration and upon temperature. For instance, Table 1 shows densities of slurries comprising NHPI in cyclohexylbenzene at NHPI concentrations of 0.1, 1.0, 5.0, 10.0, and 20.0 wt %, and also ranging from 10° C. to 100° C. (FIG. 2 is a corresponding plot of each of these slurries' densities ranging from 10-100° C.).

TABLE 1

Densities of NHPI-in-Cyclohexylbenzene (CHB) Slurries

| T(° C.) | 0 wt % NHPI in CHB $\rho_L$ (kg/m³) | 0.1 wt % NHPI in CHB $\rho_M$(kg/m³) | 1.0 wt % NHPI in CHB $\rho_M$ (kg/m³) | 5.0 wt % NHPI in CHB $\rho_M$(kg/m³) | 10.0 wt % NHPI in CHB $\rho_M$(kg/m³) | 20.0 wt % NHPI in CHB $\rho_M$ (kg/m³) |
|---|---|---|---|---|---|---|
| 10 | 951 | 951 | 954 | 968 | 986 | 1023 |
| 20 | 943 | 943 | 946 | 960 | 978 | 1016 |
| 30 | 935 | 936 | 939 | 953 | 971 | 1009 |
| 40 | 928 | 928 | 931 | 945 | 963 | 1002 |
| 50 | 920 | 920 | 923 | 938 | 956 | 995 |
| 60 | 912 | 913 | 916 | 930 | 948 | 988 |
| 70 | 905 | 905 | 908 | 922 | 941 | 981 |
| 80 | 897 | 897 | 900 | 915 | 934 | 973 |
| 90 | 889 | 890 | 893 | 907 | 926 | 966 |
| 100 | 881 | 882 | 885 | 900 | 919 | 959 |

As shown in Table 1, at 80° C., a 20.0% NHPI-in-cyclohexylbenzene slurry has density of about 973 kg/m³. As also shown in FIG. 2 and Table 1, the 20.0% NHPI-in-cyclohexylbenzene slurry's density will decrease roughly linearly with increasing temperature (e.g., at 90° C. density is 966 kg/m³; at 100° C. density is 959 kg/m³; while at 10° C. density is 1023 kg/m³) at a given NHPI concentration; on the other hand, increasing NHPI concentration means increasing density, as also shown in FIG. 2 and Table 1.

The densities of Table 1 were determined from the following formula for ideal systems of solid-in-liquid slurries (Eqn. A):

$$\rho_{slurry} = \frac{1}{\frac{\text{wt }\%_{solid}}{\rho_{solid}} + \frac{\text{wt }\%_{liq}}{\rho_{liq}}}, \quad (A)$$

where ρ is density of the slurry, solid (e.g., cyclic imide, NHPI for Table 1 data), or liquid (e.g., liquid alkylbenzene or other organic liquid, CHB for Table 1 data) as indicated. Density of the liquid $\rho_{liq}$ will generally vary with temperature; for Table 1, density of the liquid (CHB) was calculated by curve-fitting a series of density measurements vs. temperature to develop the relation $\rho_{CHB}$ at T(° C.)=958.2−0.7671*(T). Although the ideal system assumption made for Eqn. A may not hold true in all instances, it provides a good estimate for density. Ordinarily skilled artisans would readily be able to recognize other suitable methods for calculating density of a slurry, including by curve-fitting to a range of density-vs-temperature data points collected by density measurements on the slurry over a range of temperatures.

Accordingly, the cyclic imide slurry of some embodiments (particularly those in which the cyclic imide slurry is NHPI in cyclohexylbenzene) may have density in accordance with those densities shown in Table 1 and FIG. 2, depending upon the temperature and/or concentration. More generally, according to some embodiments, the density of the slurry (particularly of an NHPI-in-CHB slurry) as measured at 20° C. may be within the range from about 920 to about 1030 kg/m³ (e.g., corresponding to slurry concentration within the range from 5 to 20 wt %). Similarly, slurry density in various embodiments may be characterized as within the density ranges shown in any given row in Table 1, corresponding to a given temperature and also corresponding to any of the above-noted ranges of cyclic imide concentration.

Furthermore, calculated densities for NHPI-in-CHB slurries (or, similar calculations could be made for different cyclic imides in the same or different liquid alkylbenzenes, as the ordinarily skilled artisan will recognize) could be used in a control scheme for determining feed rate of cyclic imide and/or liquid alkylbenzene to the mixing device for formation of the slurry composition. Generally, processes of some embodiments may include measuring density and temperature of the cyclic imide slurry and controlling the feed of one or more of cyclic imide and liquid alkylbenzene to the mixing device based at least in part upon the measured density and temperature. Such control may be accomplished by determining (e.g., calculating) a cyclic imide concentration in the slurry from the measured density and temperature (e.g., using correlations such as those described above for NHPI-in-CHB slurries), and controlling feed of cyclic imide and/or liquid alkylbenzene based upon the determined cyclic imide concentration (e.g., so as to achieve greater or lower cyclic imide concentration, and/or to maintain cyclic imide concentration at the currently determined level). Measuring slurry density may be accomplished at any suitable location where it would be expected to be an accurate representation of density in the mixing vessel, which the ordinarily skilled artisan will recognize. For instance, density may be measured on-line in a recirculating fluid conduit, and/or at one or more outlets of the mixing device, and/or within the mixing device at a point expected to have suitable mixing of the slurry. Preferably, slurry density is measured on-stream in a recirculating fluid conduit, or, if none is available, at the outlet of the mixing device through which slurry will be delivered to downstream processes.

Preferably, temperature is measured at the same location (e.g., using a temperature probe), although temperature may be measured at a different location where temperature is expected to accurately reflect the temperature of the slurry at the point of density measurement (which may depend upon the precise set-up of the mixing device, and will be readily recognizable by the ordinarily skilled artisan). Most preferably, temperature is measured using a temperature probe on-stream within a recirculating fluid conduit, and/or at the outlet through which slurry will be delivered to downstream processes. Where multiple temperature probes measure temperature of the slurry at multiple locations, the temperature measurements should be averaged to determine mean temperature of the slurry.

Figure 3:
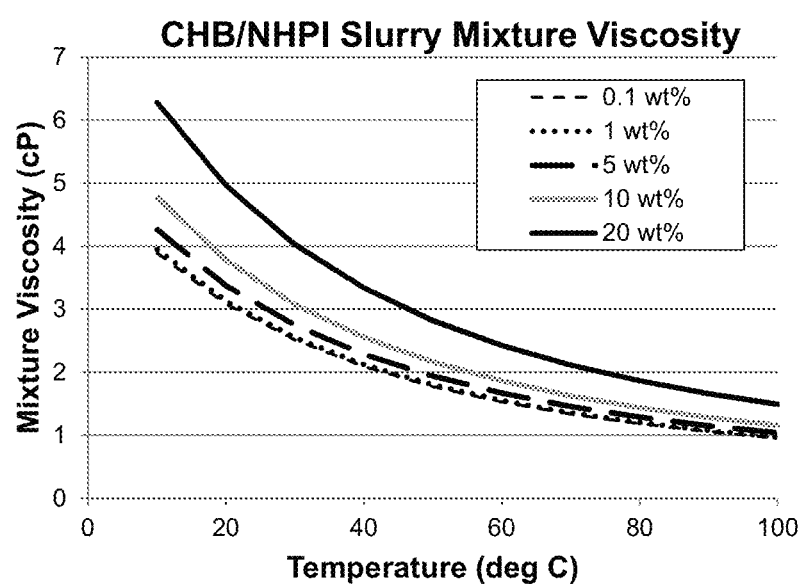
FIG. 3 is a plot of viscosity vs. temperature for NHPI-in-CHB slurries of various concentrations of NHPI, in accordance with some embodiments.

In some embodiments, slurry viscosity may also or instead be used in a manner similar to slurry density. Table 2 shows expected slurry viscosities for NHPI-in-CHB slurries of various concentrations (and FIG. 3 plots these expected values). As seen in Table 2 and FIG. 3, viscosity decreases non-linearly with increasing temperature; and, in general, greater concentration of cyclic imide means greater viscosity at a given temperature. The expected viscosities of Table 2 were determined as follows: first, volume fraction $\Phi_{solid}$ of a given wt % NHPI in CHB slurry was calculated per Eqn. (B), with reference to density of the slurry:

$$\Phi_{solid} = \rho_{slurry} * (wt\ \%_{solid}/\rho_{solid}) \qquad (B),$$

Viscosity of liquid CHB was measured at multiple temperatures and an exponential curve fit used to find that CHB viscosity varies with temperature according to the following relationship (Eqn. (C)), where T is temperature in Kelvin, and $\mu_{CHB}$ is viscosity of the CHB:

$$\mu_{CHB} = e^{\wedge}[-2.4402 + 582.73/(T-129.69)] \qquad (C),$$

Finally, the slurry viscosity $\mu_{slurry}$ as shown in Table 2 for various temperatures and wt % of NHPI was calculated based on (i) the CHB viscosity at each of the various temperatures and (ii) the volume fraction of NHPI at each of the various wt % s of NHPI, according to the following relation (Eqn. (D)):

$$\mu_{slurry} = \mu_{CHB} * (1 + 2.5 * \Phi_{solid} + 14.1 * \Phi_{solid}^2) \qquad (D),$$

Eqn. (D) is suitable for generalized slurries over a range of solid volume fractions, and could be used similarly to calculate viscosities of other solid-in-liquid slurries in accordance with various embodiments.

TABLE 2

Viscosities of NHPI-in-Cyclohexylbenzene (CHB) Slurries

| T(° C.) | 0.1 wt % NHPI in CHB $\mu_M$ (cP) | 1.0 wt % NHPI in CHB $\mu_M$ (cP) | 5.0 wt % NHPI in CHB $\mu_M$ (cP) | 10.0 wt % NHPI in CHB $\mu_M$ (cP) | 20.0 wt % NHPI in CHB $\mu_M$ (cP) |
|---|---|---|---|---|---|
| 10 | 3.89 | 3.95 | 4.26 | 4.78 | 6.28 |
| 20 | 3.08 | 3.13 | 3.38 | 3.78 | 4.96 |
| 30 | 2.51 | 2.55 | 2.75 | 3.07 | 4.02 |
| 40 | 2.09 | 2.12 | 2.28 | 2.55 | 3.34 |
| 50 | 1.77 | 1.80 | 1.94 | 2.16 | 2.82 |
| 60 | 1.53 | 1.55 | 1.67 | 1.86 | 2.42 |
| 70 | 1.34 | 1.36 | 1.46 | 1.63 | 2.11 |
| 80 | 1.18 | 1.20 | 1.29 | 1.44 | 1.86 |
| 90 | 1.06 | 1.07 | 1.15 | 1.28 | 1.66 |
| 100 | 0.96 | 0.97 | 1.04 | 1.15 | 1.49 |

As with density, then, the slurries of some embodiments may also or instead exhibit a viscosity at a given temperature approximately within the ranges set forth in Table 2 (corresponding to the concentration ranges given previously). For instance, viscosity as determined at 20° C. may be within the range from about 3.38 to about 4.96 cP (corresponding to 5-20 wt % NHPI-in-CHB). Further, processes according to some embodiments may include measuring temperature and viscosity of the slurry (instead of or in addition to measuring density of the slurry), and controlling feed of cyclic imide and/or liquid alkylbenzene to the mixing device based at least in part upon the measured temperature and viscosity. Such control may be accomplished by determining (e.g., calculating) an expected cyclic imide concentration in the slurry from the measured viscosity and temperature, and controlling feed of cyclic imide and/or liquid alkylbenzene based upon the determined cyclic imide concentration (e.g., so as to achieve greater or lower cyclic imide concentration, and/or to maintain cyclic imide concentration at the currently determined level). Viscosity measurements may be taken at any location suitable for density measurements, and are also preferably measured in a recirculating fluid conduit of the mixing device.

According to yet other embodiments, a maximum slurry viscosity may be desired to ensure the slurry is capable of being pumped. For instance, according to such embodiments, it is preferred that the slurry have viscosity less than or equal to 3300 cP, more preferably less than or equal to 1000 cP, 500 cP, or 100 cP, as measured at 25° C. For instance, viscosity may be within the range from a low of any one of 1, 2, or 3 cP to a high of any one of 10, 15, or 20 cP.

Although NHPI has been mentioned as a specific example of cyclic imides, the dry cyclic imide of various embodiments may be in accordance with the following general formula (I):

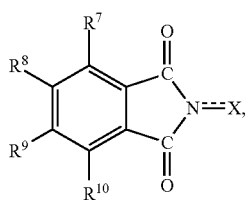

wherein X represents an oxygen atom or a hydroxyl group and each of $R^7$, $R^8$, $R^9$, and $R^{10}$ is independently selected from: (1) H; (2) $C_1$ to $C_{hd\ 20}$ hydrocarbon groups (preferably linear, branched, or cyclic alkyl groups, or aromatic groups); (3) $SO_3H$; (4) $NH_2$; (5) OH; (6) a halogen (e.g., F, Cl, Br, I); and (7) $NO_2$, provided that when any 2 adjacent R-groups are both $C_1$ to $C_{20}$ hydrocarbon groups, such adjacent R groups may be joined together to form cyclic (aliphatic or aromatic) rings. Of course, the case in which each of $R^7$, $R^8$, $R^9$, and $R^{10}$ is H, and X is a hydroxyl group, corresponds to NHPI. However, other preferred embodiments include production of a compound in which X is OH, and each of $R^7$, $R^8$, $R^9$, and $R^{10}$ is independently H or a linear, cyclic, or aromatic alkyl group having 1 to 20, more preferably 1 to 6, carbon atoms. More preferably, each of $R^7$, $R^8$, $R^9$, and $R^{10}$ is independently selected from one of: (i) H and (ii) linear or branched alkyl groups having 1 to 5, more preferably 1 to 3, carbon atoms.

Most preferably, the dry cyclic imide comprises, consists essentially of, or consists of, NHPI. In this context, "consists essentially of" means that less than 0.001 wt % of cyclic imide other than NHPI is present in the dry cyclic imide.

In some embodiments, particularly (but not necessarily) those in which the dry cyclic imide is NHPI, the dry cyclic imide may be in the form of fine needle-like crystals. These fine crystals may have diameter within the range from 5 µm to 50 µm, preferably within the range from 5 µm to 25 µm, such as 7 µm to 15 µm, with ranges from any lower limit to any upper limit also contemplated. The crystals may also or instead have length within the range from 100 µm to 600 µm, preferably 150 µm to 600 µm, such as 200 µm to 525 µm, with ranges from any lower limit to any upper limit also contemplated. Preferably, at least 70 wt %, more preferably at least 80 wt % of the cyclic imide crystals fall within the foregoing size descriptions.

The liquid alkylbenzene of the slurry may be, e.g., cyclohexylbenzene, sec-butyl benzene, cumene, ethyl benzene, sec-pentylbenzene, p-methyl-sec-butylbenzene, 1,4-diphenylcyclohexane, sec-hexylbenzene, or the like. Preferred alkylbenzenes are those having structure in accordance with the following general formula (II):

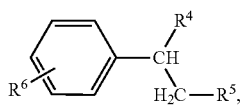

wherein $R^4$ and $R^5$ each independently represents hydrogen or an alkyl group having 1 to 4 carbon atoms, provided that $R^4$ and $R^5$ may also be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group.

The most preferred alkylbenzene is cyclohexylbenzene.

Thus, processes according to certain preferred embodiments comprise providing solid NHPI and liquid cyclohexylbenzene to a mixing device, and therein forming a slurry comprising the NHPI and cyclohexylbenzene (preferably in the wt % ranges previously described for the cyclic imide and liquid alkylbenzene, respectively).

Providing Solid Cyclic Imide to a Mixing Device

The solid cyclic imide may be obtained from any suitable source (e.g., purchase, reaction, or the like). However, processes of certain embodiments may further include synthesizing the cyclic imide and recovering solid cyclic imide. Particular examples of industrial-scale synthesis of cyclic imide and recovery of solid cyclic imide are described in International Patent Application Nos. PCT/US2017/028027 and PCT/US2017/028029, which are incorporated by reference herein. As described in those references, such processes may include: (a) continuously feeding hydroxylamine solution and a carboxylic acid anhydride to a continuous flow reactor via one or more feed inlets, so as to establish a reaction medium flowing continuously in a downstream direction within the reactor; (b) at a second location along the reactor that is downstream of the one or more feed inlets, feeding steam or water into the reaction medium; (c) at a third location along the reactor that is downstream of the second location, feeding additional steam or additional water into the reaction medium; (d) agitating the reaction medium within the reactor between the second and third locations; and (e) recovering a reaction product comprising solid cyclic imide from the reaction medium. The solid cyclic imide may then be separated from the reaction product by solid/liquid separation processes such as vacuum filtration and/or gravity filtration, or the like.

Following (a) obtaining the solid cyclic imide (whether by purchase, synthesis, or otherwise), processes according to some embodiments further comprise (b) feeding the cyclic imide to the mixing device (e.g., the slurry mix tank), forming therein a slurry in accordance with the previous description. Some embodiments also include measuring the mass flow rate of the solid cyclic imide to the mixing device, and controlling the mass flow rate based at least in part upon the measured flow rate, so as to maintain the concentration of cyclic imide in the slurry in the mixing device within the previously described desired ranges. Furthermore, feeding the cyclic imide to the mixing device may comprise: (b-1) conveying the cyclic imide to a storage vessel, (b-2) optionally storing it within the storage vessel, and (b-3) feeding it from the storage vessel to the mixing device.

Examples according to some embodiments of such processes may be illustrated with reference to FIG. 1. For instance, the storage silo 50 of FIG. 1 is an example of a storage vessel according to some embodiments. In yet other embodiments, multiple storage vessels may be employed (e.g., in series, as shown in FIG. 1 with storage silo 50 and surge hopper 90, being a smaller storage vessel utilized for mass flow control). Thus, processes according to such embodiments may include (b-1) conveying the solid cyclic imide to a first storage vessel, (b-2) conveying the solid cyclic imide from the first storage vessel to a second storage vessel (preferably having smaller volume than the first storage vessel), (c) optionally storing the cyclic imide in either or both of the first and second storage vessels, and (d)

conveying the cyclic imide from the second storage vessel to the mixing device and therein forming a slurry in accordance with the above slurry description. Some of these embodiments may further include measuring mass flow rate of the solid cyclic imide out of the second storage vessel. Certain embodiments further include controlling the mass flow rate of the solid cyclic imide to the mixing device based at least in part upon the measured mass flow rate, so as to maintain the cyclic imide within the slurry within the previously described concentration ranges.

More specific example embodiments according to FIG. 1 will now be described. Dry cyclic imide may be received in a storage container 10 (e.g., a super sack, as illustrated in FIG. 1; or another type of sealed bag, truck, solid storage vessel, or any other container suitable for powder-like solids). The dry cyclic imide is placed in a solids conveyor 20 (e.g., a pneumatic system as illustrated in FIG. 1; or, in some embodiments, a mechanical system such as a bucket loader, moving belt, vibratory device, solid screw conveyor, or the like). The solids conveyor 20 is preferably closed to the environment. Pneumatic conveying per FIG. 1 may be performed either in a dilute phase (high velocity) or dense phase (low velocity) device. Dilute phase (high velocity) is preferred due to potential plugging issues at low velocities. As illustrated in FIG. 1, an inert gas is used to pneumatically convey the solid cyclic imide through the conveying system 20 to a storage silo 50. In such a conveying system, a pump 30 is used to maintain flow of inert gas, which may be in a once-through manner or in a recirculating manner (the latter is shown in FIG. 1). The inert gas is preferably nitrogen due to low cost. Oxygen concentration in the inert gas is preferably no more than 10 vol %, more preferably no more than 8 vol %, such as no more than 5 vol %, to minimize flammability risk with the cyclic imide.

Preferably, the conveying system passes the cyclic imide through a solid filtration device 40 such as cyclones or bag houses (or a combination thereof) in order to capture small particulate fines that will not settle out easily from gravity. This helps prevent loss of solid cyclic imide into the environment surrounding the system, which can be particularly advantageous in view of safety considerations. For instance, the cyclic imide NHPI is known to cause adverse reactions such as rashes, breathing difficulty, and the like in some people. The dry cyclic imide falls from the filtration device 40 via gravity into the storage silo 50.

Alternatively, the solid cyclic imide may be received directly into a storage silo 50, without need for a conveying system 20 (although still preferably, but not necessarily, with a filtration device 40).

The storage silo 50 preferably has an interior wall finish with a low friction angle with respect to the cyclic imide. Examples include #1 Mill, #2B, or #4 180 Grit (which may also be referred to as a No. 4 Dairy or No. 4A) finishes. Also or instead, preferred finishes may be characterized in terms of their Roughness Average (RA, in microinches, as measured by ISO 1302). Preferred RA ranges from 2-50, more preferably from 4-25, or even 4-20.

Preferably, the storage silo 50 is inerted (e.g., with nitrogen or another inert gas blanket) so as to prevent formation of a flammable dust mixture inside the storage silo 50. The storage silo 50 further includes a bottom portion 52 having angled walls. Preferably, the walls are steeply angled so as to prevent cyclic imide from consolidating, while also serving to funnel the solid particles to a discharge outlet 55 at the bottom of the storage silo 50. For instance, in some embodiments, the walls have angles of 70° or less, such as 60° or less, off of vertical (i.e., measured from a vector running in the direction of gravity), preferably within a range from 5° to 60° off of vertical, such as 5° to 15° or 5° to 10° off of vertical.

A solid discharge valve 60, such as a slide valve (as illustrated in FIG. 1) is disposed below the silo discharge outlet 55 in order to isolate the silo 50 from downstream processes. A screw feeder 70 or other solid conveying device may be used to meter dry cyclic imide into a rotary valve 80, which acts as a vapor lock. The screw feeder 70 of some embodiments is equipped with protrusions on the rotating shaft to break up any agglomerated or packed cyclic imide solids.

The rotary valve 80 (or similar solid metering valve) discharges the dry cyclic imide into a surge hopper 90, which may be any suitable solid storage vessel. In some embodiments, it may be similar to the storage silo 50, but preferably on a smaller scale (e.g., smaller volume), as shown in FIG. 1. The surge hopper 90 may include a bottom portion 92 having walls sloped in accordance with the description above for the bottom portion 52 of the storage silo 50. Likewise, the surge hopper 90 may have interior wall finish in accordance with the interior wall finish described with respect to the storage silo 50. In some embodiments, the surge hopper 90 is also vented, e.g., via a gas vent conduit (not shown in FIG. 1) in fluid communication with the storage silo 50, in order to maintain proper pressure balance in the system and to maintain the solid flow. In general, pressure differential across a solid metering valve (e.g., rotary valve 80 and/or second rotary valve 120) should be at least 250 Pa gauge (about 1 in. $H_2O$ gauge). A higher pressure differential may be maintained (e.g., at least 300 Pa gauge, or at least 750 Pa gauge, or within the range from 500 to 1,000, 1,500, or 2,000 Pa gauge). This helps insure adequate flow and avoids plugging.

Disposed below the discharge outlet 95 of the surge hopper 90 is a second solid discharge valve 110, which may be, e.g., a slide valve (as illustrated in FIG. 1), similar to the solid discharge valve 60 of the storage silo 50. Preferably, the surge hopper discharge outlet 95 and/or the surge hopper 90 are equipped with a mass measuring system 100 to measure the flow of solid cyclic imide out of the surge hopper 90. Any suitable device for measuring solid mass flow may be used, such as a strain gauge, as shown in FIG. 1. Alternatively, the weight of material inside the surge hopper 90 may be measured against time, so as to measure loss and/or gain in weight over a time period (thereby allowing one to determine flow rate out of the hopper 90 while material is being discharged from the hopper 90). The solid cyclic imide is conveyed through a second solid conveyor 115 (which may be any suitable solid conveyor as described with respect to solid conveyor 70, such as a screw feeder) to the mixing device 200, preferably via a second rotary valve 120 or similar solid metering valve.

The amount of dry cyclic imide metered into the mixing device 200 is preferably controlled based at least in part upon the measured mass and/or mass flow out of the hopper 90 (e.g., as measured by the mass measuring system 100). More generally, processes and systems according to various embodiments include measuring the mass flow rate into the mixing device 200. Any suitable means for measurement of the mass flow rate at any point or points in the system may be utilized, as will be apparent to the ordinarily skilled artisan. For instance, mass flow measurements may be based upon the measured weight loss and/or gain in the surge hopper 90, and/or based upon a strain gauge disposed at the discharge outlet 92 of the surge hopper 90 (e.g., as shown in FIG. 1). Also or instead, mass flow out of the storage silo 50 may be measured in a similar manner (and, in such embodiments, the surge hopper 90 and the attendant conveying devices such as the second solid conveyor 115 and second rotary valve 120 may be omitted from the process, so as to provide for direct conveyance of solid cyclic imide from the storage hopper 50 to the mixing device 200).

Thus, more generally, some embodiments include controlling solid cyclic imide mass flow rate into the mixing device 200 based at least in part upon the measured solid cyclic imide mass flow rate. Preferably, the mass flow into the mixing device 200 is controlled so as to obtain and/or maintain cyclic imide concentration in the slurry formed in the mixing device 200 within the previously described concentration ranges. Control of the cyclic imide feed into the mixing device may also or instead be based at least in part upon density measurements on the slurry (discussed in more detail below).

Forming the Cyclic Imide Slurry Composition

Forming a slurry in a mixing device also includes providing organic liquid, such as liquid alkylbenzene (e.g., cyclohexylbenzene), to the mixing device. As shown in FIG. 1, liquid alkylbenzene is provided to the mixing device 200 via process stream 205. Other liquids may be provided instead to form the slurry (e.g., methanol or water). However, it is particularly advantageous to use at least a portion of the liquid alkylbenzene (and/or other organic liquid) that is to be oxidized using the cyclic imide as oxidation catalyst, where such further downstream oxidation processes are contemplated. This avoids the need to introduce additional impurities into the reaction process, and therefore avoids the need for downstream separations (e.g., of methanol, water, or the like). And, although water separation may be readily carried out (particularly where oxidation products would readily separate into an organic phase), water could retard the desired oxidation reaction at the concentrations required to maintain the cyclic imide slurry.

The mixing device 200 is preferably equipped with an agitator 210, such as an agitator with radial and/or axial impellers 211 that rotate during normal operation so as to prevent the cyclic imide in the slurry from settling to the bottom of the mixing device 200. Where the agitator has impellers, the liquid alkylbenzene is preferably provided at a sufficient rate to maintain the slurry level above the uppermost impeller of the mixing device 200. This flow rate will necessarily depend upon the size of the equipment and the distance from the bottom of the mixing device 200 to the top of the uppermost impeller; the ordinarily skilled artisan would readily be able to calculate the required flow rate given known mixing device size and dimensions (e.g., distance from bottom of device to the upper surface of the topmost impeller).

The mixing device 200 is preferably kept under an inert environment, such as nitrogen, in order to prohibit undesired oxidation in this part of the process. Thus, processes of some embodiments further include feeding and/or maintaining an inert gas (e.g., nitrogen), along with the organic liquid and solid cyclic imide, into the mixing device. This helps maintain an inert overhead in the mixing device, to the extent the slurry does not occupy all of the mixing device's internal volume. Also, it is preferable that the mixing device 200 be vented through an appropriate environmental control device, such as a scrubber, to knock down any dust that might otherwise enter the atmosphere. Advantageously, the organic liquid (e.g., liquid alkylbenzene, such as cyclohexylbenzene) used to form the slurry may also be used as the scrubbing medium in such an environmental control device.

Some embodiments, also in accordance with FIG. 1, further comprise recirculating at least a portion of the slurry (e.g., through recirculation stream 220). Such recirculation may advantageously help keep the slurry well-mixed. Recirculation may be accomplished by, e.g., drawing a slurry effluent stream (e.g., stream 212) from the mixing device 200, and splitting the effluent into at least two streams comprising (1) a recirculation stream 220 and (2) a feed forward stream 250, as shown in FIG. 1. The recirculation stream 220 returns slurry to the mixing device 200, and the feed forward stream 250 delivers the slurry to the oxidation reaction zone 300.

As noted previously, some embodiments further include measuring density of the slurry. As shown in FIG. 1, one convenient means of measuring slurry density includes the use of a density meter 230 on the recirculation stream 220 and/or a second density meter 240 on the feed forward stream 250. These measurements may, as noted, form at least part of the basis for control of cyclic imide feed into the mixing device 200.

Furthermore, according to some embodiments (also as shown in FIG. 1), the feed forward stream may itself be split into at least two streams, comprising (1) a slurry feed stream 260 for feeding to the oxidation reaction zone 300; and (2) a slurry recycle stream 270, which may be recycled to the mixing device 200 as shown in FIG. 1. Such a configuration may help prevent stagnant flow and potential plugging. The slurry can be pumped through any suitable pumping means 215, preferably with a positive displacement pump or another type of pump such as a centrifugal pump. With the slurry recycle stream 270 and a valve 262 on the slurry feed stream 260, slurry feed to the oxidation reaction zone 300 can be controlled in a precise manner, including shutting off the slurry feed entirely, while still maintaining circulation in the system so as to prevent plugging in the feed forward stream 250.

In addition, according to some embodiments, the feed forward stream 250 may be delivered through a fluid conduit such as a pipe with adequately high linear velocity so as to be above the settling velocity of the solid in the slurry. Minimum linear velocity needed to avoid settling may depend at least in part upon pipe diameter and wt % of solid cyclic imide in the slurry. For instance, for NHPI-in-CHB slurry, Table 3 gives minimum acceptable velocities for 1" (2.54 cm) and 2" (5.08 cm) pipe diameters for each of a 5 wt % and 20 wt % NHPI slurry, calculated based upon the following properties of NHPI-in-CHB: 1477 kg/m³ NHPI particle density; 927 kg/m³ CHB fluid density; 0.4 mm equivalent diameter (for needle-like NHPI particles); 2 cSt fluid viscosity; pipe diameter (1 or 2 inches inner diameter, as indicated); and wt % NHPI (5 or 20 wt %, as indicated).

Optionally, a safety factor may be utilized, such that operation of the system includes maintaining slurry linear velocity in conduits at greater than 1.1, 1.2, 1.3, 1.4, or even 1.5 times the minimum velocity. The amount of safety factor may vary widely depending on, e.g., design needs, process economics, and desired safety level.

TABLE 3

Minimum Linear Velocities for NHPI-in-CHB Slurries

| Pipe Diameter (in) | Weight % NHPI | Minimum Velocity (m/s) |
|---|---|---|
| 1 | 5 | 0.43 |
| 2 | 5 | 0.61 |

TABLE 3-continued

Minimum Linear Velocities for NHPI-in-CHB Slurries

| Pipe Diameter (in) | Weight % NHPI | Minimum Velocity (m/s) |
|---|---|---|
| 1 | 20 | 0.52 |
| 2 | 20 | 0.73 |

Thus, processes according to some embodiments (as illustrated in Table 3) may include ensuring the slurry (such as feed forward stream 250) is pumped through any conduit so as to maintain linear velocity (measured along the direction of fluid flow in the conduit) greater than or equal to 0.43 m/s, 0.61 m/s, 0.52 m/s or 0.73 m/s. More generally, however, the ordinarily skilled artisan with the benefit of this disclosure will readily be able to calculate minimum linear velocities for slurries with a range of different solid cyclic imide concentrations, and/or for slurries comprising different solid cyclic imide and/or liquid alkylbenzene. Accordingly, some embodiments more generally include operating the process so as to maintain velocity of the slurry in conduits above the minimum settling velocity of the slurry.

Providing the Slurry to a Gas/Liquid Oxidation Reaction

As previously referenced, the processes and systems for making cyclic imide slurry compositions disclosed herein can be used in various oxidation processes. One oxidation reaction of interest is the oxidation of alkylbenzene to an alkylbenzene-hydroperoxide. Thus, processes of some embodiments include oxidation of the alkylbenzene to a corresponding alkylbenzene-hydroperoxide. Where the alkylbenzene is in accordance with general formula (II) as set forth above, then the corresponding hydroperoxide is accordingly of the general formula (III):

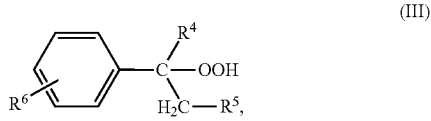

(III)

wherein $R^4$, $R^5$ and $R^6$ have the same meaning as in formula (II).

Of particular interest is the oxidation of cyclohexylbenzene (CHB) to cyclohexyl-1-phenyl-1-hydroperoxide (also referred to herein as cyclohexylbenzene hydroperoxide, or CHB-HP). Thus, in some embodiments, the alkylbenzene is cyclohexylbenzene and the corresponding hydroperoxide is cyclohexyl-1-phenyl-1-hydroperoxide.

Oxidation to form a compound according to Formula (III), such as CHB-HP, may take place in a mixed gas/liquid oxidation reaction zone. Accordingly, processes of some embodiments comprise providing the slurry of solid cyclic imide and liquid alkylbenzene to a gas/liquid oxidation reaction zone.

The gas/liquid oxidation reaction zone may comprise one or more oxidation reactors. Preferably, each oxidation reactor is suited for mixed-phase oxidation—most preferably, oxidation by contacting oxygen-containing gas (air, $O_2$, or the like) with a liquid-phase reaction medium comprising reactants (e.g., liquid alkylbenzene according to Formula (II)) and products (e.g., the desired hydroperoxide according to Formula (III)). Particularly suitable for such reactions is a bubble-column reactor with liquid and/or gas distributors, such as reactors in accordance with the description in International Patent Application Nos. PCT/US2016/035773 and PCT/US2016/035825. For instance, see ¶¶[0039]-[0089] of PCT/US2016/035773, which description is incorporated herein by reference, and/or ¶¶[0031]-[0055] of PCT/US2016/035825, which description is incorporated herein by reference. Other suitable reactors for mixed-phase gas/liquid oxidation may, however, be used in processes of various embodiments.

Figure 4:
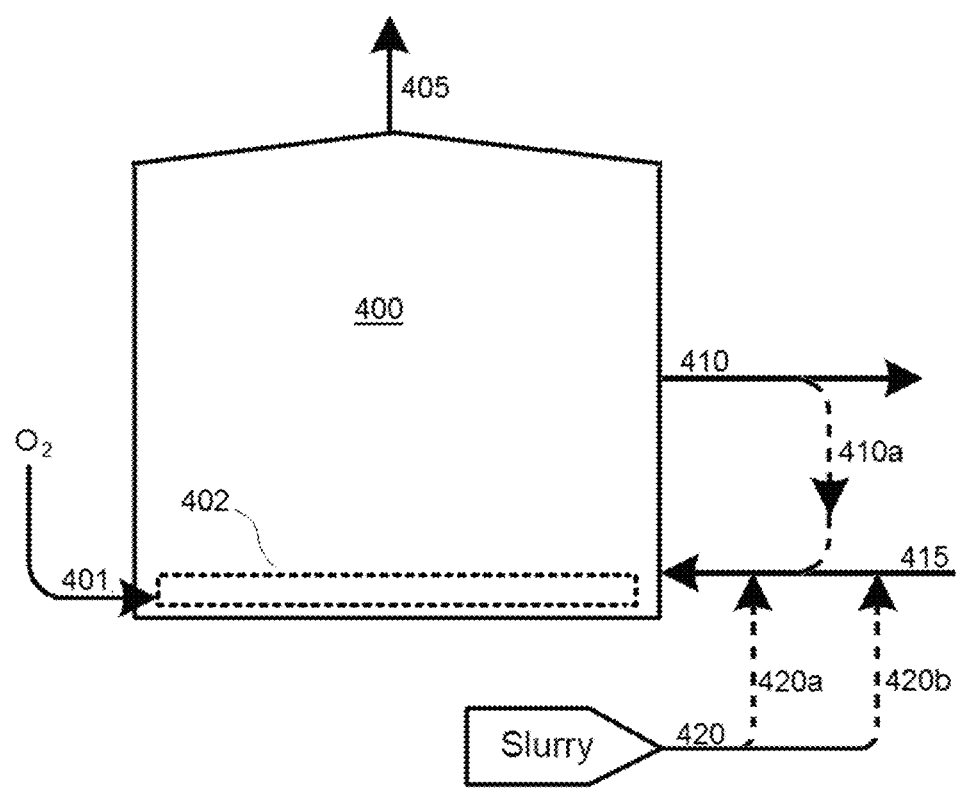
FIG. 4 is a schematic diagram of an oxidation reaction zone in accordance with some embodiments.

In some embodiments, the gas/liquid oxidation reaction zone may comprise a single oxidation reactor, such as reactor 400 shown in FIG. 4. Feed conduit 401 carries oxygen-containing gas to a gas distributor 402 disposed in a lower portion of the reactor 400. Liquid feed stream 415 comprising, e.g., liquid alkylbenzene, such as CHB is provided to the reactor 400. Optionally, the liquid may be provided through a liquid distributor disposed within the reactor 400 (e.g., as described in PCT/US2016/035773, previously incorporated by reference), not shown in FIG. 4 for the sake of simplicity. Liquid effluent stream 410 carries liquid product from the reactor 400. Optionally, an effluent recycle stream 410a may be used to recycle a portion of the effluent to the reactor 400. Preferably, the effluent recycle stream 410a mixed recycled effluent with the liquid feed stream 415, forming a combined liquid feed provided to the reactor 400 (as shown in FIG. 4). However, in some embodiments, the recycle, if present, may be provided directly back to the reactor 400 without being combined with the liquid feed (configuration not shown in FIG. 4).

A slurry feed stream 420 provides cyclic imide slurry to the reaction zone. The slurry may be fed directly to the reactor 400, but in preferred embodiments (as shown in FIG. 4), slurry is provided directly to the liquid feed stream 415. As also shown in FIG. 4, where an effluent recycle is utilized, slurry may be combined with the liquid feed stream 415 either before (conduit 420b) or after (conduit 420a) the effluent recycle is combined with the liquid feed. In yet other embodiments (not shown in FIG. 4), slurry may be provided to the effluent recycle stream 410a. It is preferred to provide the slurry to a recycle stream or to a combined effluent recycle and liquid feed stream (e.g., as shown through optional conduit 420a in FIG. 4). This is particularly so where the cyclic imide is NHPI, the liquid alkylbenzene is CHB, and the hydroperoxide is CHB-HP). The presence of hydroperoxide in the combined feed stream may increase the solubility of the cyclic imide in said combined feed, as compared to the solubility of the cyclic imide in liquid alkylbenzene alone.

Furthermore, in oxidation reactions according to some embodiments, the temperature of the recycled effluent may be greater than the temperature of the liquid feed. The combined feed will therefore also have greater temperature, and therefore increased cyclic imide solubility. Thus, although the cyclic imide slurry may be provided to the effluent recycle stream (e.g., prior to combination with the liquid feed stream), upon subsequent combination with the colder liquid feed stream, localized cold spots may form, which could result in precipitation of cyclic imide solids out of solution. Therefore, it is most preferred that the cyclic imide slurry be provided to a combined feed stream, i.e., downstream of the mixing of the liquid feed stream and the effluent recycle stream.

Summarizing the foregoing, then, processes according to some embodiments may include mixing the cyclic imide slurry with a combined liquid feed stream comprising liquid alkylbenzene and corresponding hydroperoxide so as to form a mixed feed stream. The mixed feed stream, comprising liquid alkylbenzene, corresponding hydroperoxide, and cyclic imide, is provided to the oxidation reactor; an oxygen-containing gas is also provided to the oxidation reactor, and at least a portion of the liquid alkylbenzene is oxidized to form the corresponding hydroperoxide. A liquid oxidation effluent comprising unreacted liquid alkylbenzene and corresponding hydroperoxide is withdrawn from the oxidation reactor, and a portion of the effluent is recycled and combined with a fresh liquid alkylbenzene feed stream so as to form the combined liquid feed stream.

In yet other embodiments, the oxidation reaction zone may comprise multiple oxidation reactors (e.g., in series and/or in parallel). The cyclic imide slurry may be provided to any one or more of the oxidation reactors in such embodiments. Preferably, the cyclic imide slurry is provided to each oxidation reactor. Most preferably, for each oxidation reactor in the oxidation reaction zone, the cyclic imide is mixed with a combined liquid feed stream comprising liquid alkylbenzene and corresponding hydroperoxide, forming a mixed liquid feed stream which is then provided to the oxidation reactor.

Figure 5:
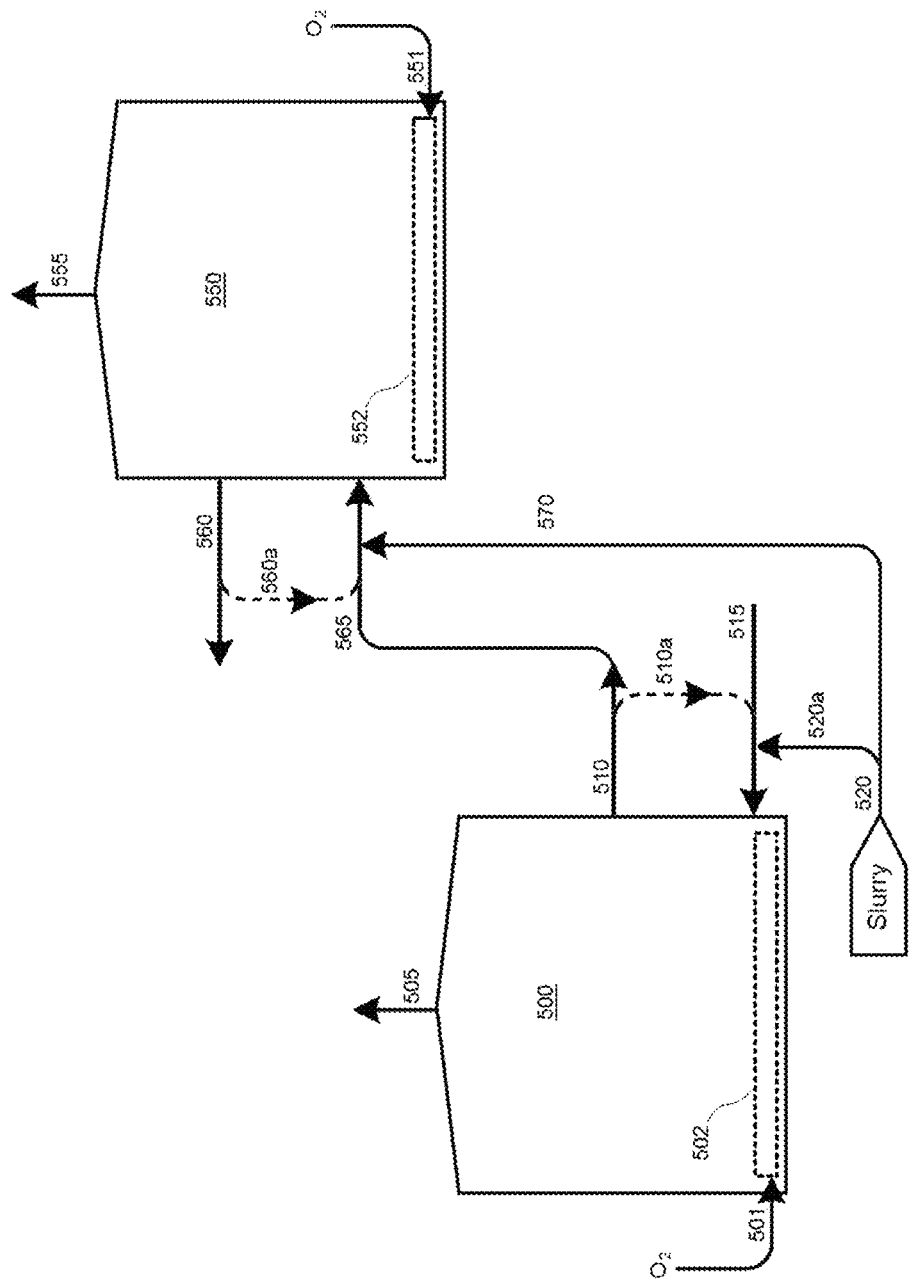
FIG. 5 is a schematic diagram of an oxidation reaction zone in accordance with further embodiments.

For instance, as shown in FIG. 5, the oxidation reaction zone may comprise two oxidation reactors 500 and 550. Oxygen-containing gas is provided to the first reactor 500 by first gas feed 501, via first gas distributor 502, and off-gas is withdrawn overhead through first overhead stream 505. Liquid alkylbenzene is fed in a first liquid feed stream 515, and liquid product leaves the first reactor 500 as first liquid effluent stream 510. A portion of the effluent may be recycled (e.g., in first recycle stream 510a) to be provided to the first liquid feed stream 515, forming a combined feed stream to the first reactor 500.

The first reactor effluent is provided to the second reactor 550 as second liquid feed stream 565 (in fluid communication with the first effluent stream 510). Oxygen-containing gas is provided by second gas conduit 551 via second gas distributor 552; off-gas is withdrawn overhead as second overhead stream 555. Liquid product is withdrawn from the second reactor 550 as the second effluent stream 560. A portion may be recycled as a second recycle stream 560a, mixed with the second feed stream 565 to form a combined feed stream.

The slurry is provided to the reaction zone in a slurry stream 520, and in particular is provided to both the first and second reactors 500 and 550. As shown in FIG. 5, a first slurry stream 520a is mixed with the first liquid feed stream 515, preferably (as shown in FIG. 5) downstream of where the first recycle stream 510a combines with the first liquid feed stream 515. Second slurry stream 570 provides additional slurry to be mixed with the second liquid feed stream 565, again downstream of where the second liquid feed stream 565 combines with the second recycle stream 560a. In yet further embodiments, slurry may be provided to three, four, or more oxidation reactors in a similar manner.

Figure 6:
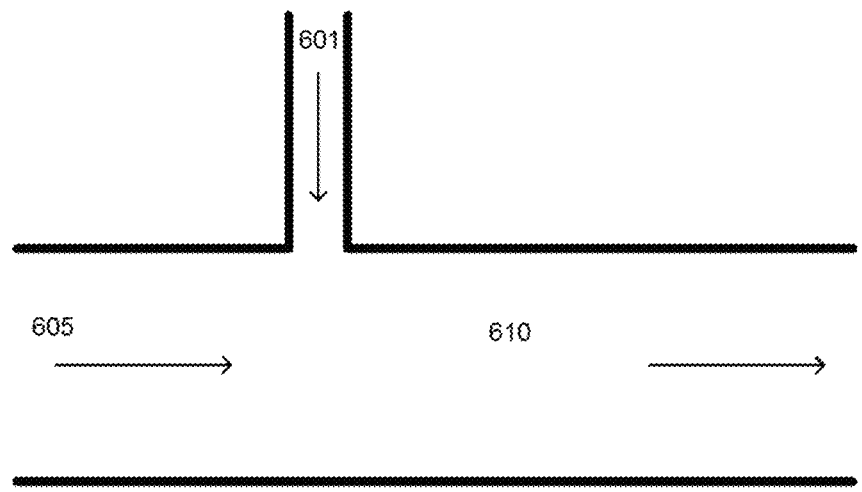
FIG. 6 is a schematic diagram of a mixing tee for mixing a cyclic imide slurry with a liquid stream in accordance with some embodiments.
Figure 7:
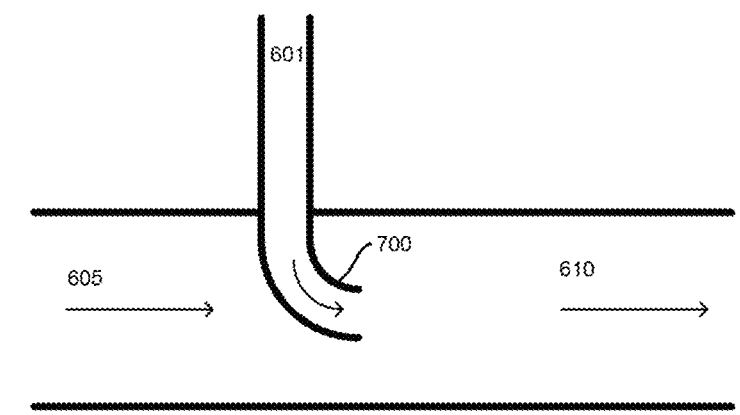
FIG. 7 is a schematic diagram of a nozzle for mixing a cyclic imide slurry with a liquid stream in accordance with some embodiments.
Figure 8:
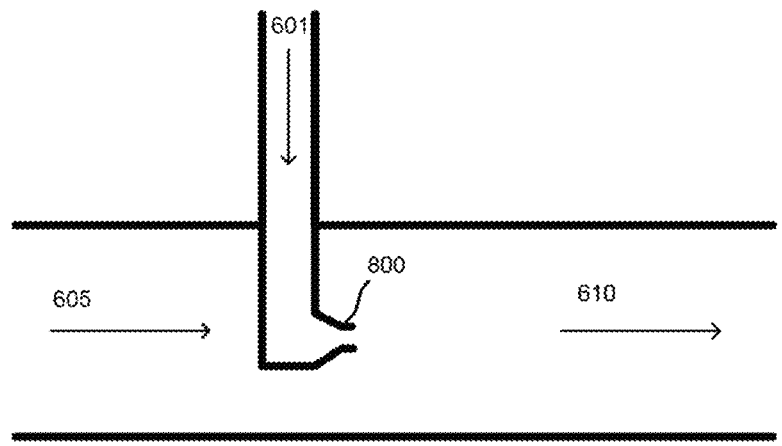
FIG. 8 is a schematic diagram of a spray nozzle for mixing a cyclic imide slurry with a liquid stream in accordance with some embodiments.
Figure 9:
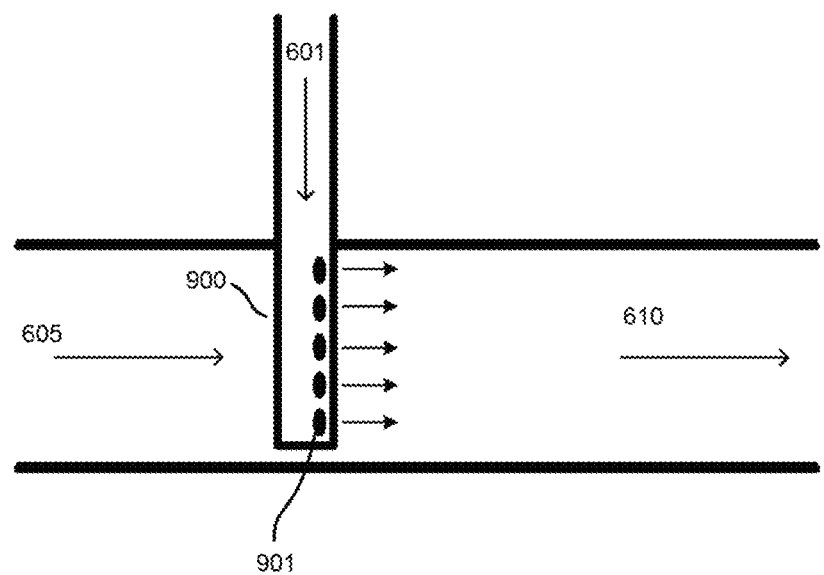
FIG. 9 is a schematic diagram of a quill with orifices for mixing a cyclic imide slurry with a liquid stream in accordance with some embodiments.

A slurry feed stream may be combined with a liquid stream (e.g., a liquid feed stream, combined feed stream, and/or effluent recycle stream) in any suitable manner. For instance, the slurry feed may be combined with the liquid stream by way of a mixing tee (e.g., as shown in FIG. 6, in which slurry stream 601 is combined with liquid stream 605 to form mixed stream 610 in a simple tee; arrows in FIG. 6 indicate direction of fluid flow). Processes according to some embodiments, on the other hand, include mixing the slurry stream 601 with a liquid stream 605 through a nozzle 700 (FIG. 7); a spray nozzle 800 (FIG. 8); or a quill 900 with orifices 901 (FIG. 9). One of these latter mixing mechanisms may advantageously obtain rapid blending to enable fast dissolution of the cyclic imide. This is particularly so where the liquid stream comprises liquid alkylbenzene and the corresponding hydroperoxide, e.g., in a recycle stream and/or a combined recycle and liquid feed stream, as discussed above, such that the cyclic imide is more readily dissolved in the liquid stream. Preferably, at least 80 wt %, more preferably at least 90 wt %, and most preferably all of the cyclic imide is dissolved in the liquid stream before reaching the oxidation reactor. This is particularly helpful in embodiments wherein a liquid stream is provided to the oxidation reactor through a liquid distributor; in such a manner, the cyclic imide achieves substantially uniform distribution throughout the oxidation reactor. Further aids to enhance in-line blending of slurry and liquid stream include orifice plates, venture constrictions, and/or static mixers.

Oxidizing Cyclohexylbenzene in the Production of Phenol and/or Cyclohexanone from Benzene As previously noted, one preferred oxidation reaction is oxidation of CHB to CHB-HP (e.g., using a slurry of cyclic imide, preferably NHPI, in CHB). Such reaction is of particular interest when integrated into a process to produce cyclohexanone and/or phenol from benzene via hydroalkylation, as described in, e.g., WIPO Publication Nos. 2014/137623 and WO 2016/053583, and summarized in more detail hereinbelow.

According to such embodiments, the cyclohexylbenzene provided to the oxidation reaction and used to form the cyclic imide slurry can be produced and/or recycled as part of an integrated process for producing phenol and cyclohexanone from benzene. Thus, processes of some embodiments may include obtaining cyclohexylbenzene from benzene, obtaining a cyclic imide slurry composition (e.g., by any of the methods described herein), and providing the cyclohexylbenzene, the cyclic imide slurry composition, and an oxygen-containing gas to an oxidation reaction zone so as to produce an oxidation effluent comprising cyclohexylbenzene-hydroperoxide. Such processes may further include contacting the oxidation effluent with a cleavage catalyst so as to obtain a cleavage effluent comprising phenol and cyclohexanone.

In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction (1) to produce cyclohexylbenzene (CHB):

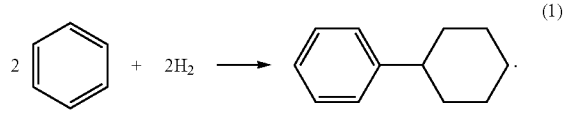 [SMILES: c1ccccc1 ; c1ccc(C2CCCCC2)cc1]

(1)

Alternatively, cyclohexylbenzene can be produced by direct alkylation of benzene with cyclohexene in the presence of a solid-acid catalyst such as molecular sieves in the MCM-22 family according to the following Reaction (2):

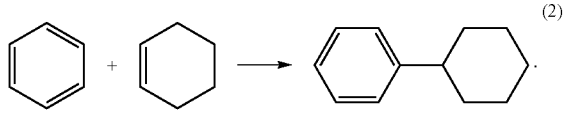

(2)

Side reactions may occur in Reaction (1) or Reaction (2) to produce some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants Thus, typically, after the reaction, the hydroalkylation reaction product mixture is separated by distillation to obtain a $C_6$ fraction containing benzene, cyclohexane, a $C_{12}$ fraction containing cyclohexylbenzene and methylcyclopentylbenzene, and a heavies fraction containing, e.g., $C_{18}$s such as DiCHBs and $C_{24}$s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step. Depending on the quantity of the heavies fraction, it may be desirable to either (a) transalkylate the $C_{18}$s such as DiCHB and $C_{24}$s such as TriCHB with additional benzene, or (b) dealkylate the $C_{18}$s and $C_{24}$s to maximize the production of the desired monoalkylated species.

Details of feed materials, catalyst used, reaction conditions, and reaction product properties of benzene hydroalkylation, and transalkylation and dealkylation, can be found in, e.g., Paragraphs [0031], [0032]-[0034], and [0036]-[0048] of WIPO Publication No. 2016/053583, which description is incorporated by reference herein.

At least a portion of liquid cyclohexylbenzene (e.g., obtained per the processes described above) is fed to a mixing device along with cyclic imide (e.g., NHPI) so as to form the cyclic imide slurry, which in turn is provided to an oxidation reaction zone. Optionally, a further portion of the liquid cyclohexylbenzene may be provided directly to the oxidation reaction zone. The cyclic imide slurry may be provided to the oxidation reaction zone separately from the further portion of liquid cyclohexylbenzene, or it may be provided to the liquid cyclohexylbenzene to form a combined feed of (i) slurry and (ii) the further portion of liquid cyclohexylbenzene into the oxidation reaction zone.

In the oxidation reaction zone, the cyclohexylbenzene is contacted with the cyclic imide oxidation catalyst (e.g., NHPI), whereupon at least a portion of the cyclohexylbenzene is converted to cyclohexyl-1-phenyl-1-hydroperoxide, the desired hydroperoxide, according to the following Reaction (3):

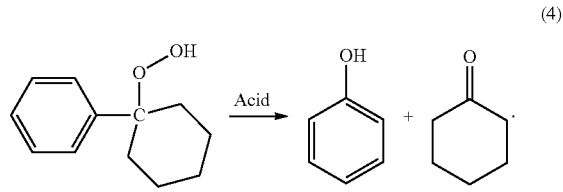

(3)

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

In exemplary processes, the oxidation may be accomplished by contacting an oxygen-containing gas, such as air and various derivatives of air, with the feed comprising cyclohexylbenzene. For example, a stream of pure $O_2$, $O_2$ diluted by inert gas such as $N_2$, pure air, or other $O_2$-containing mixtures can be pumped through the cyclohexylbenzene-containing feed in an oxidation reactor to effect the oxidation.

Details of the feed material, reaction conditions, reactors used, product mixture composition and treatment, and the like, of the oxidation can be found in, e.g., Paragraphs [0049]-[0071] of WIPO Publication No. 2016/053583, which description is incorporated by reference herein.

Subsequent Cleavage Reaction

At least a portion of the cyclohexyl-1-phenyl-1-hydroperoxide may in some embodiments be subsequently contacted with an acid catalyst so as to decompose at least a portion of the cyclohexyl-1-phenyl-1-hydroperoxide to cyclohexanone and phenol according to the following desired Reaction (4):

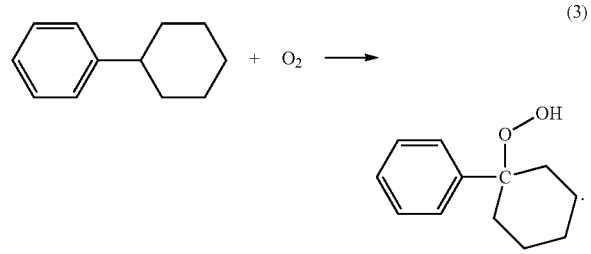

(4)

The cleavage product mixture may comprise the acid catalyst, phenol, cyclohexanone, cyclohexylbenzene, and contaminants.

The acid catalyst preferably is at least partially soluble in the cleavage reaction mixture, is stable at a temperature of at least 185° C., and has a lower volatility (higher normal boiling point) than cyclohexylbenzene.

Feed composition, reaction conditions, catalyst used, product mixture composition and treatment thereof, and the like, of this cleavage step can be found in, e.g., Paragraphs [0072]-[0084] of WIPO Publication No. 2016/053583, which description is incorporated by reference herein.

Further processing of the cleavage product mixture, e.g., to obtain phenol and/or cyclohexanone products, may take place as described in Paragraphs [0085]-[0127] of WIPO Publication No. 2016/053583, which description is incorporated by reference herein.

Alternative Oxidation Reactions and Slurry Compositions

Solid cyclic imides such as NHPI have also been reported as useful in oxidation of hydrocarbons, such as cyclohexane to cyclohexanone and/or cyclohexanol. Likewise, NHPI may be suitable for oxidation of alcohols, such as the oxidation of cyclohexanol to cyclohexanone.

Therefore, certain embodiments are further contemplated whereby, instead of an alkylbenzene, solid cyclic imide slurry compositions are formed with more general hydrocarbons (e.g., cyclohexane) than the sub-set of alkylbenzenes. In particular, the slurry may be formed with liquid cyclohexane, which in turn is intended to be oxidized (using the cyclic imide as a catalyst) to form cyclohexanol and/or cyclohexanone.

As yet another alternative, the solid cyclic imide slurry composition may be formed using an organic alcohol, preferably a $C_3$ to $C_{10}$ linear or cyclic organic alcohol (in particular cyclohexanol), instead of the alkylbenzenes previously discussed. The slurry of such embodiments may, for instance, be formed using liquid cyclohexanol instead of the above-discussed liquid alkylbenzene, and the cyclohexanol subsequently oxidized so as to form cyclohexanone. The processes described herein would otherwise be very similar, such that processes according to these embodiments are carried out like the embodiments utilizing alkylbenzenes, except that the alkylbenzene is replaced with a more generic hydrocarbon (e.g., cyclohexane) or an organic alcohol (e.g., a $C_3$ to $C_{10}$ linear or cyclic organic alcohol, such as cyclohexanol). Wt % of cyclic imide in slurries comprising a liquid hydrocarbon (e.g., cyclohexane) or a liquid organic alcohol (e.g., a $C_3$ to $C_{10}$ linear or cyclic organic alcohol such as cyclohexanol) would be similar to the cases described above for cyclic imide in liquid alkylbenzene, although densities and viscosities would be different from the liquid alkylbenzene case. Nonetheless, with the methods described herein, one could readily determine expected densities and/or viscosities of such slurries in order to apply similar control techniques based on density and/or viscosity measurements as previously discussed with respect to cyclic imide in liquid alkylbenzene slurries. Formation of cyclic imide slurries in the manner described herein would provide substantial advantages in industrial-scale operation of such alternative oxidation reactions.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. The contents of all references cited herein are incorporated by reference in their entirety.

The invention claimed is:

1. A process comprising:
   (a) feeding a solid cyclic imide and a liquid alkylbenzene to a mixing device;
   (b) within the mixing device, forming a slurry comprising 3 wt % to 45 wt % of the solid cyclic imide in the liquid alkylbenzene;
   (c) providing the slurry and an oxygen-containing gas to a mixed gas/liquid oxidation reaction zone; and
   (d) oxidizing at least a portion of the alkylbenzene in the mixed gas/liquid oxidation reaction zone in the presence of the cyclic imide, thereby forming a corresponding alkylbenzene-hydroperoxide; and
   further comprising measuring the temperature of the slurry and one or both of density and viscosity of the slurry, and controlling the feed of solid cyclic imide and/or liquid alkylbenzene into the mixing device based at least in part upon the measured temperature and measured density and/or viscosity, so as to form the slurry comprising 3 wt % to 45 wt % of the solid cyclic imide.

2. The process of claim 1, wherein the cyclic imide has the general formula (I):

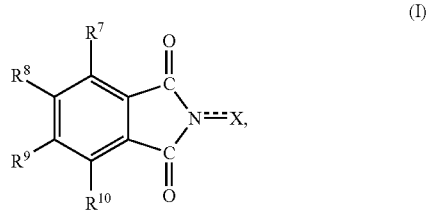

where, in formula (I), X is an oxygen atom or a hydroxyl group, and further wherein each of $R^7$, $R^8$, $R^9$, and $R^{10}$ is independently selected from: (1) H; (2) $C_1$ to $C_{20}$ linear, cyclic, or aromatic hydrocarbon groups; (3) $SO_3H$; (4) $NH_2$; (5) OH; (6) a halogen; and (7) $NO_2$.

3. The process of claim 2, wherein the cyclic imide is N-hydroxyphthalimide (NHPI).

4. The process of claim 1, wherein the alkylbenzene has the general formula (II), and the alkylbenzene-hydroperoxide has the general formula (III):

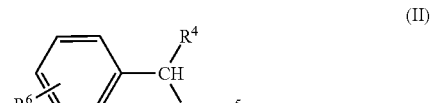

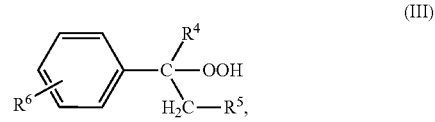

where, in each general formula (II) and (III), $R^4$ and $R^5$ are each independently selected from hydrogen or an alkyl group having from 1 to 4 carbon atoms, provided that $R^4$ and $R^5$ may also be joined to form a cyclic group having from 4 to 10 carbon atoms, said cyclic group being optionally substituted, and $R^6$ is selected from the group consisting of hydrogen, one or more alkyl groups having from 1 to 4 carbon atoms, and a cyclohexyl group.

5. The process of claim 4, wherein the alkylbenzene is cyclohexylbenzene, and the alkylbenzene-hydroperoxide is cyclohexyl-1-phenyl-1-hydroperoxide.

6. The process of claim 5, further comprising:
   (a-1) contacting benzene with hydrogen under hydroalkylation conditions in the presence of a hydroalkylation catalyst to produce cyclohexylbenzene;
   (a-2) feeding a first portion of the cyclohexylbenzene to the mixing device; and
   (a-3) feeding a second portion of the cyclohexylbenzene to the oxidation reaction zone.

7. The process of claim 1, further comprising measuring mass flow rate of the solid cyclic imide fed into the mixing device, and controlling the feed of solid cyclic imide into the mixing device based at least in part upon the measured mass flow rate, so as to form the slurry comprising 3 wt % to 45 wt % of the solid cyclic imide.

8. The process of claim 1, wherein the slurry comprises 10 wt % to 30 wt % solid cyclic imide in liquid alkylbenzene.

9. The process of claim 1, wherein the slurry comprises at most 0.1 wt % of impurities.

10. The process of claim 1, further comprising recirculating at least a portion of the slurry out of and back into the mixing device.

11. The process of claim 1, further comprising feeding an inert gas to the mixing device so as to maintain an inert overhead environment in the mixing device.

12. The process of claim 1, wherein providing the slurry to the mixed gas/liquid oxidation reaction zone comprises mixing the slurry with a combined liquid feed stream comprising liquid alkylbenzene having general formula (II) and corresponding hydroperoxide having general formula (III) so as to form a mixed feed stream, and providing the mixed feed stream to an oxidation reactor.

13. The process of claim 12, wherein the combined liquid feed stream is formed by recycling a portion of a liquid oxidation effluent stream to be combined with a liquid alkylbenzene feed stream.

14. The process of claim 1, wherein providing the slurry to the mixed gas/liquid oxidation reaction zone comprises mixing the slurry with a liquid stream by way of a mixing tee, a nozzle, a spray nozzle, or a quill with orifices.

15. A process comprising:
(a) feeding a solid cyclic imide and liquid cyclohexane to a mixing device;
(b) within the mixing device, forming a slurry comprising 3 wt % to 45 wt % of the solid cyclic imide in the liquid cyclohexane;
(c) providing the slurry and an oxygen-containing gas to a mixed gas/liquid oxidation reaction zone; and
(d) oxidizing at least a portion of the cyclohexane in the mixed gas/liquid oxidation reaction zone in the presence of the cyclic imide, thereby forming cyclohexanol and/or cyclohexanone; and
further comprising measuring temperature of the slurry and one or both of density and viscosity of the slurry, and controlling the feed of solid cyclic imide and/or liquid cyclohexane into the mixing device based at least in part upon the measured temperature and measured density and/or viscosity, so as to form the slurry comprising 3 wt % to 45 wt % of the solid cyclic imide.

16. A process comprising:
(a) feeding a solid cyclic imide and liquid organic alcohol to a mixing device;
(b) within the mixing device, forming a slurry comprising 3 wt % to 45 wt % of the solid cyclic imide in the liquid organic alcohol;
(c) providing the slurry and an oxygen-containing gas to a mixed gas/liquid oxidation reaction zone; and
(d) oxidizing at least a portion of the alcohol in the mixed gas/liquid oxidation reaction zone in the presence of the cyclic imide; and
further comprising measuring the temperature of the slurry and one or both of density and viscosity of the slurry, and controlling the feed of solid cyclic imide and/or liquid liquid organic alcohol into the mixing device based at least in part upon the measured temperature and measured density and/or viscosity, so as to form the slurry comprising 3 wt % to 45 wt % of the solid cyclic imide.

17. The process of claim 16, wherein the organic alcohol is cyclohexanol.

18. The process of claim 15, wherein the cyclic imide has the general formula (I):

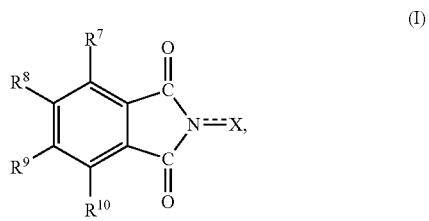

where, in formula (I), X is an oxygen atom or a hydroxyl group, and further wherein each of $R^7$, $R^8$, $R^9$, and $R^{10}$ is independently selected from: (1) H; (2) $C_1$ to $C_{20}$ linear, cyclic, or aromatic hydrocarbon groups; (3) $SO_3H$; (4) $NH_2$; (5) OH; (6) a halogen; and (7) $NO_2$.

19. The process of claim 15, wherein the cyclic imide is N-hydroxyphthalimide (NHPI).

* * * * *